United States Patent [19]

Yamamoto et al.

[11] Patent Number: 5,714,591
[45] Date of Patent: Feb. 3, 1998

[54] GADOLINIUM-DTPA COMPLEX CONTAINING CARBORANE UNIT, INTERMEDIATES THEREOF AND METHOD OF SYNTHESIZING THEM

[75] Inventors: Yoshinori Yamamoto, Sendai; Hisao Nemoto, Tokushima, both of Japan

[73] Assignee: President of Tohoku University, Sendai, Japan

[21] Appl. No.: 682,004

[22] Filed: Jul. 16, 1996

[30] Foreign Application Priority Data

Jul. 21, 1995 [JP] Japan .................. 7-185307

[51] Int. Cl.$^6$ .................. C07F 5/00; C07F 5/02; A61K 49/00; A61K 51/00
[52] U.S. Cl. .................. 534/16; 568/4; 564/8; 424/1.65; 424/9.364
[58] Field of Search .................. 424/1.65, 9.364; 534/16; 564/8; 568/4

[56] References Cited

U.S. PATENT DOCUMENTS

| 4,959,356 | 9/1990 | Miura et al. .................. 514/64 |
| 5,286,853 | 2/1994 | Spielvogel et al. .................. 534/16 |

FOREIGN PATENT DOCUMENTS

| 0 700 918 | 3/1996 | European Pat. Off. . |
| WO 94/06805 | 3/1994 | WIPO . |

OTHER PUBLICATIONS

Progress in Neutron Capture Therapy for Cancer, pp. 231–233, 1992, A.D. Whittaker, et al., "Synthesis of $^{10}$B–and $^{157}$Gd–Labelled DNA Ligands for Neutron Capture Therapy".
Phys. Med. Biol., 1992, vol. 37, No. 1, pp. 155–162, Tetsuo Matsumoto, "Transport Calculations of Depth–Dose Distributions for Gadolinium Neutron Capture Therapy".
Tetrahedron Letters, vol. 37, No. 4, pp. 539–542, Jan. 22, 1996, Hisao Nemoto, et al., "A New Synthetic Method of All Carboxylate–Free DTPA Derivatives and its Application to the Synthesis of Gd–Carborane Complex".
1995 International Chemical Congress, Dec. 17–22, 1995, abstract of the presentation by Dr. Jianping Cai, et al., "Synthesis of All Carboxylate–Free DTPA Derivatives Via Palladium Catalyzed Carbon–Carbon Bond Formation Reaction".

Database WPI, Derwent Publications, AN 96–175722, JP–A–8 053 475, Feb. 27, 1996.

*Primary Examiner*—John Kight
*Assistant Examiner*—Lara C. Kelley
*Attorney, Agent, or Firm*—Oblon, Spivak, McClelland, Maier & Neustadt, P.C.

[57] ABSTRACT

The present invention provides a gadolinium-DTPA complex containing a carborane unit having structural formula (1) given below and an intermediate thereof, i.e., carborane-containing DTPA derivative represented by formula (2) given below.

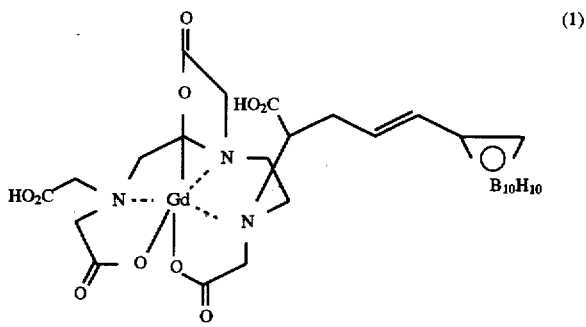

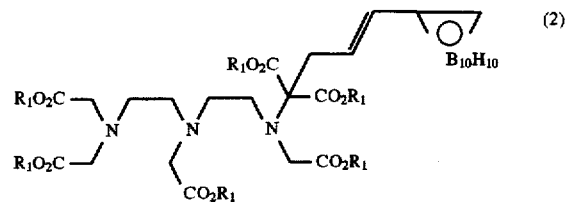

The present invention also provides a method of synthesizing the compound (1), which comprises reacting an ester derivative of DTPA with a carborane derivative in the presence of a palladium catalyst, deesterifying by treatment with an acid, reacting with gadolinium trichloride hexahydrate, and treating with an alkali to give the desired compound (1).

9 Claims, No Drawings

GADOLINIUM-DTPA COMPLEX CONTAINING CARBORANE UNIT, INTERMEDIATES THEREOF AND METHOD OF SYNTHESIZING THEM

BACKGROUND OF THE INVENTION

1. Field of the Invention

The present invention relates to a gadolinium-DTPA (diethylene triamine pentaacetic acid) complex containing a carborane unit, intermediates thereof, and method of synthesizing them. Particularly, the present invention is directed to a gadolinium-DTPA complex effective for use as medicines relating to MRI and as a neutron capture agent used in a radiotherapy of cancers.

2. Description of the Related Art

Neutron capture therapy is included in the radiotherapy of cancers. In the neutron capture therapy, mercaptoundecahydrodecaborate (BHS) and para-boronophenyl alanine (BPA) are particularly used as a neutron capture agent in the treatment of brain tumor and malignant skin cancer. In the neutron capture therapy using these boron compounds, these boron compounds are administered to the patient by means of intravenous injection or direct injection into the diseased part, and after a period of time, thermal neutrons are irradiated to the diseased part. For improving the therapeutic effect, it is strongly required that the diseased part is irradiated with thermal neutrons when the boron compound is accumulated at the tumor in the patient in the highest concentration. However, it is practically difficult to measure consecutively the boron concentration of the compound in each tissue in a body, leading to reduction in the therapeutic effect.

On the other hand, a gadolinium-DTPA complex, which is commercially available under the trade name of "Magnebist" and used in recent years as an MRI contrast medium, attracts particularly high attentions in the medical field (Sieving, P. F., Watson, A. D., and Rocklage, S. M., "Gadolinium complexes for paramagnetically active protein conjugates", Bioconjugate Chem., 1990, 1, 65).

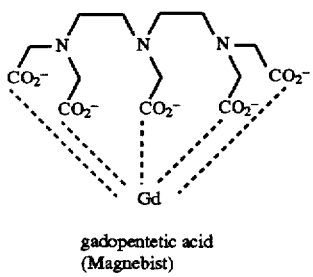

gadopentetic acid
(Magnebist)

A method for using DTPA complex as a medicament by modification of introducing a biological active site into DTPA has also been studied (Bailey M. P., Rocks B. F., Riley C., "Lanthanide complexes for measurement of optical purity by NMR," Analyst, 1984, 109, 1449).

Hitherto, the modification of DTPA has been performed by binding a biological active site to one of five carbonyl groups of DTPA by an ester bond or an amide bond as shown in the following formulas (Wenzel, T. J., Bogyo, M. S. and Lebeau, E. L., J. Am. Chem. Soc., 1994, 116, 4858; Sieving, P. F., Watson, A. D., and Rocklage, S. M., "Gadolinium complexes for paramagnetically active protein conjugates," Bioconjugate Chem., 1990, 1, 65; Bailey, M. P., Rocks B. F., Riley C., "Lanthanide complexes for measurement of optical purity by NMR." Analyst, 1984, 109, 1449; Paik C. H., Sood, V. K., Le, N., Cioloca, L., Carrasquillo, J. A., Reynolds, J. C., Neumann, R. D., Rega, R. C., "Radioactive indidum complexes bearing antibodies," Nucl. Med. Biol., 1992, 19, 517.).

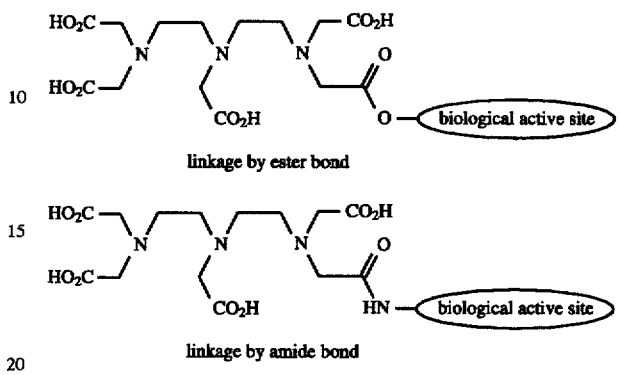

linkage by ester bond linkage by amide bond

In such a modification method of DTPA, one of five carboxyl groups of DTPA is converted into an ester or an amide. Consequently, the carboxyl groups capable of coordinating to a metal ion is reduced in number to four. Such reduction of number of the carboxyl groups may result in a lowering DTPA coordination ability, and lead to a problem in that a metal ion is liberated in vivo (Deshpanda S. V., Subramanian, R., McCall, M. J., DeNardo, G. L., Meares, C. F., J. Nuclear Med., 1990, 31, 218; Meares, C. F., McCall, M. J., Reardan, D. T., Goodwin, D. A., Diamanti, C. I., Mctigue, M., Anal. Biochem., 1984, 142, 68; Meares, C. F., Goodwin, D. A., J. Protein Chem., 1984, 3, 215.).

The present invention has been made in view of the aforementioned problem and is intended to provide a gadolinium-DTPA complex containing a carborane unit, which permits consecutively measuring the accumulation amount of the boron carriers in a tumor tissue by means of MRI, since the complex is linked a gadolinium-DTPA complex (Magnebist) used as MRI contrast medium for a medical treatment to a boron compound, particularly a carborane unit.

Another object of the present invention is to provide an intermediate of a gadolinium-DTPA complex containing a carborane unit.

Still another object is to provide a method of synthesizing a gadolinium-DTPA complex containing a carborane unit and an intermediate thereof.

SUMMARY OF THE INVENTION

According to a first aspect of the present invention, there is provided a gadolinium-DTPA complex containing a carborane unit, wherein one of its plane structure is represented by the following formula (1):

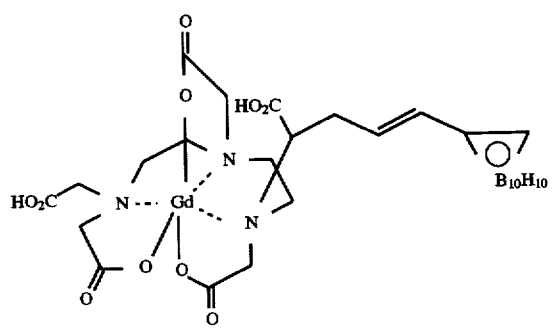

(1)

According to a second aspect of the present invention, there is provided a carborane-containing DTPA derivative, which is represented by following formula (2):

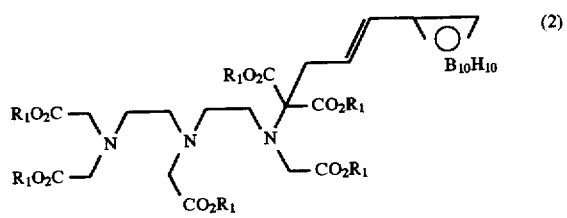

(2)

wherein $R_1$ is hydrogen or a lower alkyl group.

According to a third aspect of the present invention, there is provided a carborane-containing DTPA derivative, which has a structure of following formula (2a):

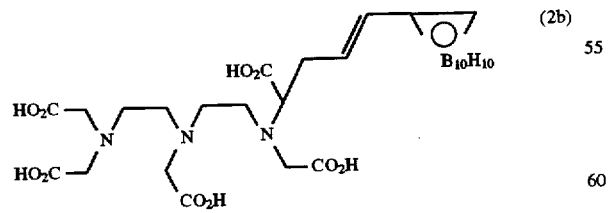

(2a)

According to a fourth aspect of the present invention, there is provided a carborane-containing DTPA derivative, which has a structure represented by following formula (2b):

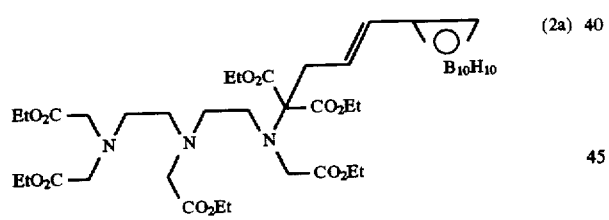

(2b)

According to a fifth aspect of the present invention, there is provided a method of synthesizing a gadolinium-DTPA complex containing a carborane unit, wherein one of its plane structure is represented by following formula (1).

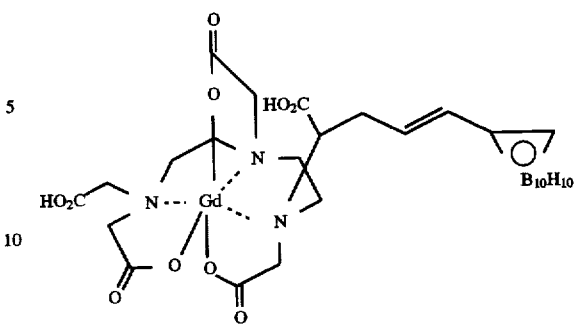

(1)

The method of the present invention comprises the steps of:

(a) reacting an ester derivative of DTPA (3) with a carborane derivative (4) in the presence of a palladium catalyst and an organic phosphine to give a carborane-containing DTPA derivative (2c), as shown below:

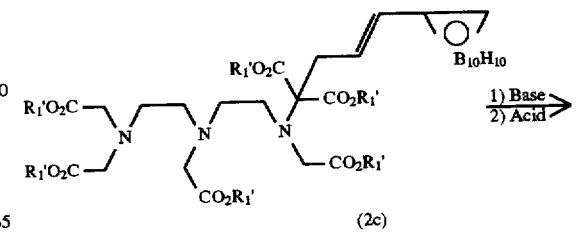

where R and $R_1'$ are a lower alkyl group;

(b) treating the carborane-containing DTPA derivative (2c) obtained in step (a) with a base, followed by deesterification by treatment with an acid to give a compound (2b), as shown below:

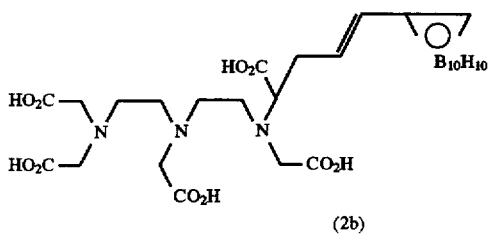

(2b)

where $R_1'$ is a lower alkyl group; and (c) reacting the compound (2b) obtained in step (b) with gadolinium trichloride hexahydrate, followed by treatment with an alkali to give a gadolinium-DTPA complex containing a carborane unit, as shown below.

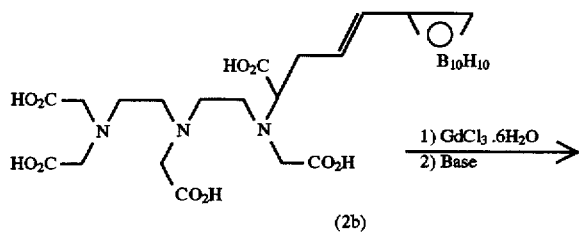

(2b)

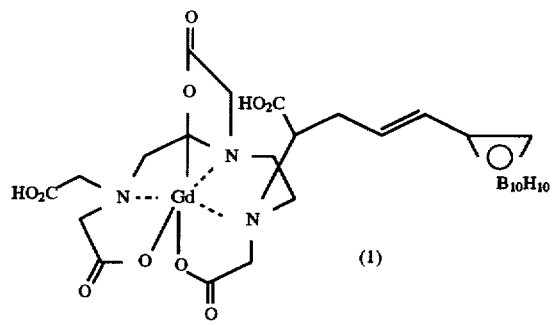

(1)

According to a sixth aspect of the present invention, there is provided a method of synthesizing a carborane-containing DTPA derivative which is represented by formula (2c), comprising a reaction of an ester derivative of DTPA (3) with a carborane derivative (4) in the presence of a palladium catalyst and an organic phosphine to give the compound (2c), as shown below:

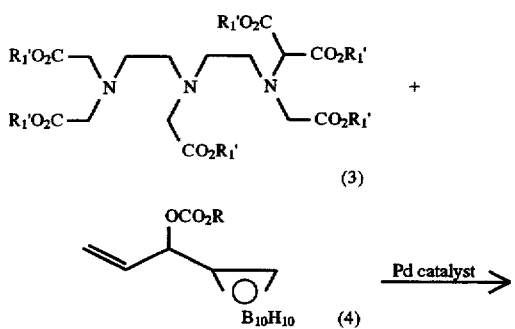

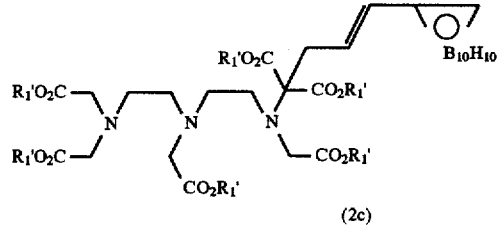

(2c)

where R and $R_1'$ are a lower alkyl group.

Further, according to a seventh aspect of the present invention, there is provided a method of synthesizing a carborane-containing DTPA derivative, which has a following formula (2b).

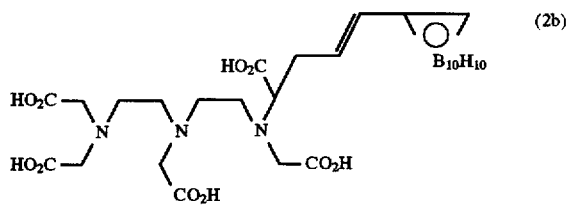

(2b)

The method comprises the steps of:

(a) reacting an ester derivative of DTPA (3) with a carborane derivative (4) in the presence of a palladium catalyst and an organic phosphine to give a carborane-containing DTPA derivative (2c), as shown below:

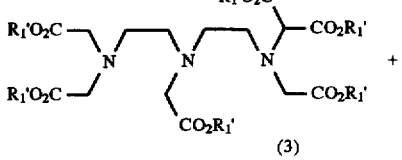

(3)

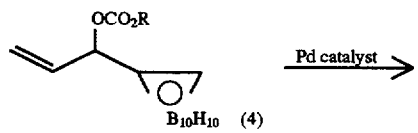

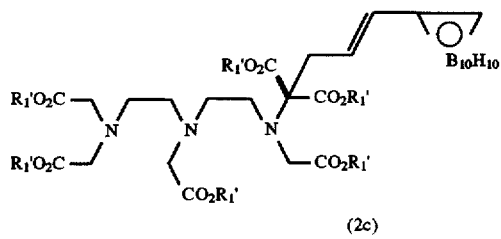

(2c)

where R and $R_1'$ are a lower alkyl group; and (b) treating carborane-containing DTPA derivative (2c) obtained in step (a) with an alkali, followed by deesterification by treatment with an acid to give a compound (2b), as shown below:

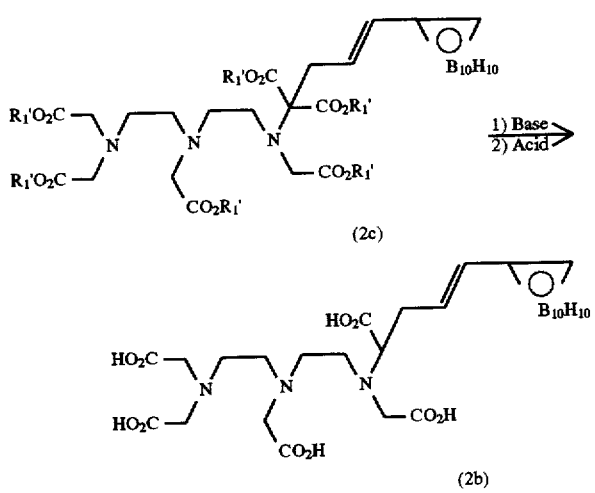

(2c)

(2b)

where $R_1'$ is a lower alkyl group.

The gadolinium-DTPA complex containing a carborane unit, provided by the present invention, permits consecutively measuring the accumulation amount of the boron carriers in a tumor tissue by MRI. In addition, since the complex contains gadolinium having itself a large neutron capture cross section like boron, the complex of the present invention is expected to produce a strong lethal toxicity against cancer cell, compared with the conventional neutron capture agent containing a carborane unit alone. Further, since the complex of the present invention has five free carboxyl groups, the coordination to a metal ion is stronger than in the conventional DTPA derivative in which an active site such as a carborane unit is introduced by an ester bond or an amide bond.

Further, compound (2a) in which $R_1$ is an ethyl group and compound (2b) in which $R_1$ is a hydrogen, in the compound (2) are important intermediates used in the synthesis of compound (1). Also, these compounds (2a) and (2b) themselves can be used as effective neutron capture agents.

DETAILED DESCRIPTION OF THE PREFERRED EMBODIMENT

The present invention provides a gadolinium-DTPA complex containing a carborane unit. The complex of the present invention is featured in that a carborane unit is attached to the —$CH_2$— group included in one of —$CH_2COOH$ groups on N atom at the end of DTPA, and that three carboxyl groups and three nitrogen atoms in the molecule form a complex with a gadolinium metal ion as shown in formula (1). In other words, compound (1) of the present invention forms a complex between DTPA with five free carboxyl groups and a gadolinium metal ion, and has a carborane unit attached to DTPA by means of non-ester bond.

On the other hand, the carborane-containing DTPA derivative (2) of the present invention is featured in that an alkyloxycarbonyl group and a carborane unit are attached to the —$CH_2$— group of one of —$CH_2COOR_1$ groups on N atom at the end of DTPA. Because of such characteristics, the compound (2) has a specific feature in that an organic group can be introduced by non-ester bond, with five carboxylic groups of DTPA remaining unchanged.

Compound (2) of the present invention can be used as an important intermediate in the synthesis of compound (1). Also, compound (2) which is a carborane derivative, itself can be used as a neutron capture agent in the treatment of cancers.

$R_1$ in formula (2) represents hydrogen or a linear or branched lower alkyl group having 1 to 6 carbon atoms. Specific examples of $R_1$ include hydrogen, methyl, ethyl, n-propyl, isopropyl, n-butyl, sec-butyl, tert-butyl, n-pentyl, n-hexyl groups and the like, but $R_1$ is not limited to these examples. Preferably, $R_1$ is hydrogen or ethyl group.

The gadolinium-DTPA complex containing a carborane unit, which is provided by the present invention, permits consecutively measuring the accumulation amount of the boron carriers in a tumor tissue by MRI. In addition, since the gadolinium-DTPA complex contains gadolinium having itself a large neutron capture cross section like boron, the complex of the present invention is expected to produce a strong lethal toxicity against cancer cell, compared with the conventional neutron capture agent containing a carborane unit alone. Further, since the complex of the present invention has five free carboxyl groups, the coordination to a metal ion is stronger than in the conventional DTPA derivative in which an active site such as a carborane unit is introduced by an ester bond or an amide bond.

Further, compound (2a) in which $R_1$ is an ethyl group and compound (2b) in which $R_1$ is a hydrogen, in the compound (2) are important intermediates used in the synthesis of compound (1). Also, these compounds (2a) and (2b) themselves can be used as effective neutron capture agents.

Hereinbelow, the method of synthesizing the compounds of the present invention will be explained in detail.

In the following methods, $R_1'$ represents a linear or branched lower alkyl group having 1 to 6 carbon atoms. Specific examples of $R_1'$ include methyl, ethyl, n-propyl, isopropyl, n-butyl, sec-butyl, tert-butyl, n-pentyl, n-hexyl groups and the like, but $R_1'$ is not limited to these groups. Preferably, $R_1'$ is an ethyl group.

R represents a linear or branched lower alkyl group having 1 to 6 carbon atoms including, for example, methyl, ethyl, n-propyl, isopropyl, n-butyl, sec-butyl, tert-butyl, n-pentyl, and n-hexyl groups, but R is not limited to these examples. Preferably, R is methyl, ethyl, or sec-butyl group.

The method of synthesizing compound (1) will be explained below.

In step (a), carborane unit is introduced into compound (3). In this step, compound (3) is reacted with carborane derivative (4) in the presence of a palladium catalyst such as palladium.(dibenzylideneacetone)$_2$ [Pd(dba)$_2$)] and 1,2-bis (diphenylphosphino)ethane (dppe). The reaction is carried out in an etherial solvent such as THF. The palladium catalyst employed is used in an amount of 5 to 15 mol %, preferably 10 mol %, based on the amount of compound (3). The amount of carborane derivative (4) is used in amount of 2 to 4 equivalents, preferably 2.5 to 3 equivalents, based on the amount of compound (3). The reaction temperature is from 50° to 150° C., preferably 50° to 100° C., more preferably 50° to 80° C. The reaction time is 1 to 20 hours, preferably 1 to 10 hours, more preferably 1 to 5 hours. In the present invention, as a catalyst, Pd2(dba)$_3$.CHCl$_3$ may be used in place of the aforementioned Pd(dba)$_2$. Further, other organic phosphines such as triphenylphosphine, trimethylolpropane phosphite and the like can also be used in the present invention in place of dppe. However, dppe is most preferable.

Compound (2c) obtained in the step (a) can be separated and purified by an appropriate manner such as a silica gel column chromatography or recrystallization. In this step, the carborane unit can be selectively introduced into compound (3) by use of the Pd catalyst.

Incidentally, compound (3) used as a reactant in step (a) can be prepared by the process given below:

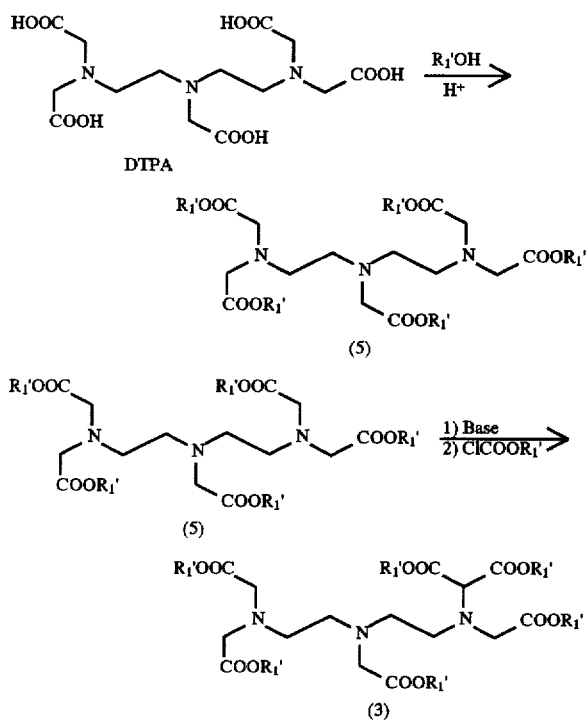

where $R_1'$ is as defined above.

In the first step, the carboxyl groups of DTPA are protected by esters. In the esterification, a conventional esterification reaction may be used. For example, the esterification is performed in the presence of acid. To be more specific, DTPA is treated in an alcohol as a solvent in the presence of a strong acid such as concentrated sulfuric acid, concentrated hydrochloric acid, or p-toluenesulfonic acid. The alcohol used is not particularly restricted. A lower alcohol is preferably used, more preferably methanol, ethanol, propanol and the like, and most preferably ethanol. Since the alcohol used also acts as a solvent, other solvent is not required. However, if necessary, a solvent may be used. In any case, an alcohol must be used in excess. The preferred alcohol to be used is an absolute alcohol. A reaction temperature may preferably be at an appropriate temperature ranging from 50° C. to a reflux temperature of the alcohol employed. A preferred reaction time may be from 1 to 24 hours. After completion of the reaction, the resultant reaction solution is made basic with an aqueous alkaline solution such as an aqueous sodium hydroxide. The obtained product (5) can be separated and purified by appropriate manner such as silica gel column chromatography or recrystallization.

In the next step, an alkoxy carbonyl group is introduced into the resultant product of pentaester derivative (5) to give compound (3). In this step, the pentaester derivative (5) is treated with a base such as potassium bis(trimethylsilyl) amide (KBMSA), lithium diisopropylamide or sodium bis (trimethylsilyl)amide, and then treated with an alkyl chloroformate wherein the alkyl group is the same lower alkyl group as defined above $R_1$. Preferable examples of the alkyl chloroformate include methyl chloroformate, ethyl chloroformate, propyl chloroformate, and the like. The most preferable example is ethyl chloroformate. The alkyl chloroformate is used in an amount of 2 to 4 equivalents, preferably 2.5 to 3 equivalents, based on the amount of compound (5). The reaction is carried out by using an etherial solvent such as diethyl ether or THF. The reaction temperature is −60° to −80° C., preferably at −78° C. The treatment with a base is carried out for 20 minutes to 2 hours. The treatment with an alkyl chloroformate is performed for 20 minutes to one hour. The compound (3) can be separated and purified by appropriate manner such as silica gel column chromatography or recrystallization.

The method of synthesizing compound (1) of the present invention also comprises step (b) in which the carborane-containing DTPA derivative (2c) obtained in step (a) is converted into a compound (2b) which has five free carboxyl groups by hydrolysis and simultaneous decarboxylation of one carboxyl group on the carbon atom attached with the carborane unit by the hydrolysis treatment.

The hydrolysis of ester may be performed by a conventional deesterification reaction. To more specific, compound (2c) is treated, for example, in an aqueous alcohol solution of lithium hydroxide, then acidified with a diluted acid such as 1N hydrochloric acid to afford compound (2c). The hydrolyzing reaction is carried out at 0° to 50° C., preferably at 10° to 25° C. The reaction time is 1 to 20 hours, preferably 1 to 10 hours. The resultant compound (2c) can be separated and purified by appropriate manner such as silica gel column chromatography or recrystallization.

Incidentally, the carborane derivative (4) was prepared from a compound (6) and an alkyl chloroformate dissolved in halosolvent such as a dichloromethane by adding a solution of pyridine in halosolvent at −10° C. and stirring for about 3 hours, as shown below. The compound (6) is prepared by a method using o-carborane as a starting material, described in "J. L. Mauer, F. Verchier, A. J. Serino, C. B. Knobler and M. F. Hawthorne, J. Org. Chem., 55, 838–843 (1990)":

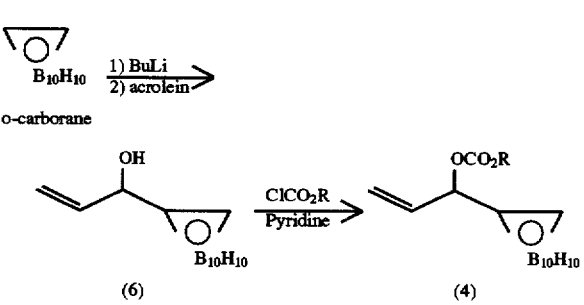

where, R is as defined above.

Further, the method of synthesizing compound (1) of the present invention comprises step (c) in which the carborane-containing DTPA derivative (2b) obtained in step (b) is coordinated to a gadolinium metal ion. In this step (c), gadolinium trichloride hexahydrate is added to an alcohol solution of the carborane-containing DTPA derivative (2b) in an equimolar amount to the derivative (2b), followed by treating the resultant mixture with a base to afford a desired product of a gadolinium-DTPA complex containing carborane unit. The reaction between the carborane-containing DTPA derivative (2b) and gadolinium trichloride hexahydrate is carried out at 0° to 50° C., preferably at room temperature. The alcohol used is not particularly limited. A lower alcohol is preferably used, more preferably methanol, ethanol, propanol or butanol and the like, and most preferably methanol. The reaction time is 1 to 24 hours, preferably 1 to 10 hours, and most preferably 2 to 5 hours. On the other hand, an alkali metal carbonate such as sodium carbonate, potassium carbonate, sodium hydrogen carbonate or potassium hydrogen carbonate can may be used as an effective alkali in the subsequent step of an alkali treatment.

The resultant gadolinium-DTPA complex containing carborane unit (1) can be purified by means of HPLC with methanol-water, etc. as an eluent.

From the foregoing, it is clear that the compound (1) of the present invention can be synthesized through the aforementioned steps.

The present invention also provides a method of synthesizing a carborane-containing DTPA derivative (2c), and the method will be explained in detail below.

The compound (2c) can be synthesized the same procedure as in step (a) in the method of synthesizing the compound (1). The compound (2c) can be synthesized by the reacting the compound (3) with the carborane derivative (4) in the presence of a palladium catalyst such as Pd(dba)$_2$ and an organic phosphine, e.g. dppe. Another palladium catalyst such as Pd$_2$(dba)$_3$.CHCl$_3$ can also be used in the present invention. Further, other organic phosphines such as triphenylphosphine and trimethylolpropane phosphite can also be used in place of dppe. However, dppe is most preferable as the organic phosphine. By this reaction, a carborane unit can be selectively introduced into the compound (3). The resultant compound (2c) can be separated and purified by appropriate manner such as silica gel column chromatography or recrystallization.

Further, the present invention provides a method of synthesizing the carborane-containing DTPA derivative (2b), and the method will be explained in detail below.

The method comprises steps (a) and (b), which are similar to steps (a) and (b) in the method of synthesizing the compound (1) of the present invention. In step (a), the reaction between the compound (3) and the carborane derivative (4) is carried out in the presence of a palladium catalyst such as Pd(dba)$_2$ and an organic phosphine, e.g. dppe. The reaction conditions in step (a) are similar to those in step (a) in the method of synthesizing the compound (1). Another palladium catalyst such as Pd$_2$(dba)$_3$.CHCl$_3$ can also be used in step (a). Further, other organic phosphines such as triphenylphosphine and trimethylolpropane phosphite can also be used in place of dppe, but it is most desirable to use dppe as the organic phosphine. By this reaction, a carborane unit can be selectively introduced into the compound (3).

In step (b) of the synthesizing method of the compound (2b), the compound (2c) obtained in step (a) is hydrolyzed and simultaneous decarboxylation of one carboxyl group on the carbon atom with attached carborane unit by the hydrolysis treatment. The reaction conditions in step (b) are also similar to the conditions in step (b) in the synthesizing method of the compound (1). The reaction product (2b) can be separated and purified by appropriate manner such as silica gel column chromatography or recrystallization.

EXAMPLES

Hereinbelow, the present invention will be described in detail by way of Example, which should not be construed as limiting the scope of the present invention.

In the following Examples, we will explain the present invention with reference to the case of the compound where R$_1$ represents an ethyl group. Various alternations and modifications may be made by one skilled in the art, but such alternations and modifications will be included in the scope of the preset invention.

Preparations

Preparation of Pentaethyl Ester of DTPA (5a)

25 g (63.5 mmol) of diethylene triamine pentaacetic aced (DTPA) and 10 ml (180 mmol) of a concentrated sulfuric acid were dissolved in 500 ml of absolute ethanol, and the resultant mixture was refluxed for 20 hours. The reaction mixture was concentrated, and the resulting residue was diluted with methylene chloride. Ten percent aqueous solution of NaOH was added to the reaction solution at 0° C. to make the solution alkaline. Then, an organic layer was separated, dried over anhydrous MgSO$_4$ and filtrated. The filtrate was concentrated, and then purified by silica gel column chromatography with hexane:ethyl acetate=2:3 as an eluent to give 26.88 g (50.4 mmol, yield of 78.3%) of a pure ethyl ester (5a):

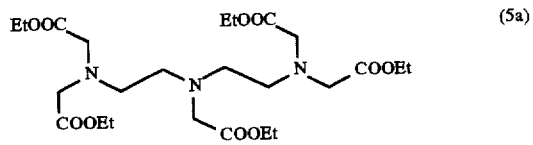

IR (Film): 2979s, 1735s, 1029s, 728m cm$^{-1}$. $^1$H-NMR (CDCl$_3$): δ (ppm) 4.21–4.1 (m, 10H), 3.57 (s, 8H), 3.49 (s, 2H), 2.9–2.75 (m, 8H), 1.27 (t, J=7.5 Hz, 12H), 1.26 (t, J=7.5 Hz, 3H). $^{13}$C-NMR (CDCl$_3$): δ (ppm) 171.5(q), 171.2(q), 60.3(d), 60.1(d), 55.2(d), 52.7(d), 52.2(d), 14.2(s), Anal. Cal. for C$_{24}$H$_{43}$N$_3$O$_{12}$: C 54.02, H 8.12, N 7.87; found C 53.79, H 7.88, N 7.72.

Preparation of Compound (3a)

0.5M toluene solution of potassium bis(trimethylsilyl) amide (15 ml, 7.5 mmol) and THF were added to a 100 ml flask cooled to −78° C. under a nitrogen atmosphere. To this solution, a compound (5a) obtained in the above step (a) (2 g, 3.75 mmol) in 30 ml of THF was slowly added dropwise over a period of 12 minutes. After the reaction mixture was stirred for 70 minutes at −78° C., ethyl chloroformate (1.22 g, 11.25 mmol) in 30 ml of THF was dropwise over a period of 20 minutes. The resulting mixture was further stirred for 50 minutes. The reaction was quenched by adding aqueous 2N NH$_4$Cl solution and ether which were previously cooled. The resultant reaction mixture was extracted with ether, dried over anhydrous MgSO$_4$, and filtrated. The filtrate was concentrated to give a crude product which was purified by silica gel column chromatography with benzene:ethyl acetate=2:1 as an eluent to afford 1.2 g (1.98 mmol, yield of 78.3%) of compound (3a) as pure form:

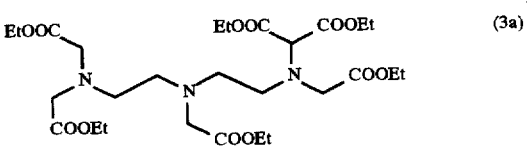

IR (Film): 2980s, 1728s, 1034s, 728m cm$^{-1}$. $^1$H-NMR (CDCl$_3$): δ (ppm) 4.48 (s, 1H), 4.27–4.06 (m, 12H), 3.67 (s, 2H), 3.56 (s, 4H), 3.48 (s, 2H), 2.97–2.73 (m, 8H), 1.33–1.2 (m, 18H). $^{13}$C-NMR (CDCl$_3$): d (ppm) 171.6(q), 171.3(q), 168.4(d), 168(q), 67.5(t), 61.4(d), 61.5(d), 60.4(d), 60.2(d), 55.2(d), 55.1(d), 53.5(d), 53.2(d), 52.7(d), 52.3(d), 51.5(d), 14.5(s). Anal. Cal. for C$_{27}$H$_{47}$N$_3$O$_{12}$: C 53.54, H 7.82, N 6.94; found C 53.36, H 7.51, N 6.78.

Preparation of Carborane Derivative (4)

(i) preparation of Compound (4a), where R=Isobutyl Group

A solution of compound (6) (541 mg, 2.7 mmol), prepared by a method using o-carborane as a starting material (see J. L. Mauer, F. Verchier, A. J. Serino, C. B. Knobler and M. F. Hawthorne, J. Org. Chem., 55, 838–843 (1990)) and pyridine (1.4 ml) in 5 ml of methylene chloride was added to a solution of iso-butyl chloroformate (1.11 g, 8.1 mmol) in 5 ml of methylene chloride at −10° C. under a nitrogen atmosphere.

After being stirred for 3 hours, the reaction mixture was poured into an ice-water. Then, an organic layer was extracted, dried over anhydrous MgSO$_4$, filtrated, and concentrated. The resulting crude product was purified by silica gel column chromatography with hexane:ethyl acetate=1:1 as an eluent to give a pure compound (4a) (653.4 mg, 2.18 mmol, 80.6%).

IR (Film): 3072s, 2966s, 2595s, 1750s, 1646m, 1471s, 1019s, 720 scm$^{-1}$; $^1$H-NMR (CDCl$_3$): δ 5.83–5.68(m, 1H), 5.52 (d, J=7.5 Hz, 1H), 5.48–5.38 (m, 2H), 3.96 (dd, J=2.5, 6.5 Hz, 1H), 3.95 (dd, J=2.5, 6.5 Hz, 1H), 3.87 (s, 1H), 2.07–1.90 (m, 1H), 0.95 (d, J=6.5 Hz, 6H) ppm. $^{13}$C-NMR (CDCl$_3$): δ 153.5(q), 131.2(t), 121.7(d), 76.8(t), 75.1(d), 74.7(q), 59.2(t), 27.8(t),18.9(s) ppm. Anal. cal. for C$_{10}$H$_{24}$B$_{10}$O$_3$, C 39.98, H 8.05; found C 40.28, N 7.75.

(ii) Preparation of Compound (4b), where R=Ethyl Group 1.48 g (5.44 mmol, yield of 91%) of compound (4b) was obtained as in above (i) using 1.20 g (5.98 mmol) of compound (6), 1.95 g (17.93 mmol) of ethyl chloroformate, and 2.9 ml of pyridine.

IR (Film): 3072s, 2985s, 2593s, 1752s, 1645m, 1002s cm$^{-1}$, $^1$H-NMR (CDCl$_3$): δ 5.82–5.67 (m, 1H), 5.51 (d, J=7.5 Hz, 1H), 5.48–5.38 (m, 2H), 4.23 (q, J=7 Hz, 2H), 3.87 (s, 1H), 1.33 (t, J=7 Hz, 3H) ppm; $^{13}$C-NMR (CDCl$_3$): δ 153.3(q), 131.2(t), 121.9(d), 76.9(t), 74.7(q), 65.3(t), 59.3 (d), 14.1(s) ppm; Anal. cal. for C$_8$H$_{20}$B$_{10}$O$_3$, C 35.28, H 7.4; found C 35.08, N 7.16.

(iii) Preparation of Compound (4c), where R=Methyl Group 1.44 g (5.57 mmol, yield of 77.2%) of compound (4c) was obtained as in above (i) using 1.45 g (7.23 mmol) of compound (6), 2.05 g (21.7 mmol) of methyl chloroformate, and 3.8 ml of pyridine.

IR (Kbr): 3080s, 2970m, 2590s, 1720s, 1650w, 1440s, 1250s, 720s cm$^{-1}$; $^1$H-NMR (CDCl$_3$): δ 5.82–5.67 (m, 1H), 5.51 (d, J=7.5 Hz, 1H), 5.48–5.40 (m, 2H), 3.58 (s, 1H), 3.83 (s, 3H) ppm. $^{13}$C-NMR (CDCl$_3$): δ 153.9(q), 131.0(t), 122.0(d), 77.0(t), 74.5(q), 59.2(t), 55.6(s) ppm. Anal. cal. for C$_7$H$_{18}$B$_{10}$O$_3$, C 32.55, H 7.02; found C 32.6, N 6.8.

Example

Synthesis of Compound (2a)

One equivalent of compound (3a), 0.1 equivalent of Pd(dba)$_2$, 0.2 equivalent of dppe and 3 equivalents of compound (4) were dissolved in THF, and the resultant mixture was refluxed for 12 hours under a nitrogen atmosphere. After removal of THF, the mixture was purified by silica gel column chromatography with hexane:ethyl acetate:methanol=40:20:1 to give a pure compound (2).

Further, compound (2a) was synthesized by using compounds (4a) to (4c) prepared above, with the results as shown in Table 1:

TABLE 1

| entry | Compound (4) (mg/mmol) | Compound (3a) (mg/mmol) | Pd(dba)$_2$ (mg/mmol) | dppe (mg/mmol) | Compound (2a) (mg/mmol) (yield) |
|---|---|---|---|---|---|
| 1 R=i-Bu | (4a) (31.9/1.04) | 214.6/0.353 | 20.4/0.0035 | 28.2/0/07 | 107.2/0.136 (38.4%) |
| 2 R=Et | (4b) (578.9/2.89) | 584.2/0.96 | 55.2/0.096 | 76.5/0/19 | 562.2/0.71 (74.3%) |
| 3 R=Me | (4c) (1144/4.43) | 894.2/1/48 | 84.9/0.148 | 117.6/0/30 | 747.1/2.84 (64.2%) |

Synthesis of Compound (2b)

A solution of LiOH-H$_2$O (558.2 mg, 13.3 mmol) in 30 ml of ethanol was added to a solution of compound (2a) (1.16 g, 1.47 mmol) in 5 ml of ethanol over a period of 30 minutes at room temperature, and the resultant mixture was stirred for 12 hours. The reaction mixture was filtered through Celite, and the ethanol was removed from the filtrate to give a residue which was then diluted with 15 ml of water. To this solution was added ether to remove impurities insoluble in water. To the resulting mixture was added an aqueous solution of hydrochloric acid (10.8%, 4.5 g, 13.3 mmol) at 0° C. to make the reaction solution acidic. After the acidic solution was stirred for 20 minutes, the precipitate was collected, dissolved in 20 ml of methanol, and purified by HPLC with MeOH-H$_2$O (5:2) as an eluent to give 547.8 mg (0.998 mmol) of compound (2b) with a yield of 67.9%.

IR (KBr): 3411m, 3014s, 2592s, 1726s, 1632s, 1396s, 1222s, 1018m cm$^{-1}$; $^1$H-NMR (CDCl$_3$): δ 6.17 (dt, J=7, 15.5 Hz, 1H), 5.89 (d, J=15.5 Hz, 1H), 4.62 (s, 1H), 4.06–3.88 (m, 1H), 3.62 (s, 4H), 3.53–3.08 (m, 12H), 2.65–2.4 (m, 2H) ppm; $^{13}$C-NMR(CDCl$_3$): δ 175.7(q), 174.5(q), 174.1(q), 170.4(q), 136.3(t), 127.7(d), 75.1(q), 65.3(t), 62.4(t), 56.1 (d), 55.7(d), 53.9(d), 53.8(d), 53(d), 50.7(d), 50.3(d), 33.3 (d). Anal. cal. for C$_{19}$H$_{37}$B$_{10}$N$_3$O$_{10}$·½ H$_2$O, C 39.04, H 6.55, N 7.19; found C 38.96, H 6.43, N 7.05.

Synthesis of Gadolinium-DTPA complex containing Carborane unit (1)

139.7 mg (0.374 mmol) of GdCl$_3$·6H$_2$O was added to a solution of compound (2c) (215.4 mg, 0.374 mmol) in 5 ml of methanol with stirring at room temperature, and further stirred for 5 hours. To this solution was added 31.4 mg (0.374 mmol) of $Na_2CO_3$, and the resultant mixture was stirred for 30 minutes at room temperature. The reaction mixture was diluted with 5 ml of MeOH, and purified by HPLC with MeOH-$H_2O$ as an eluent to give 152.7 mg (0.209 mmol) of compound (1) with a yield of 55.9%.

IR (Kbr) 3375m, 2980m, 2592s, 1596s, 1405s, 1094s, 1021m, 723m $cm^{-1}$; Anal. cal. for $C_{19}H_{37}B_{10}N_3O_{10}Gd.¼$ $H_2O$. C 31.08, H 4.74, N 5.72; found C 31.45, H 4.77, N 5.33.

What is claimed is:

1. A gadolinium-DTPA complex containing a carborane unit represented by the following formula (1):

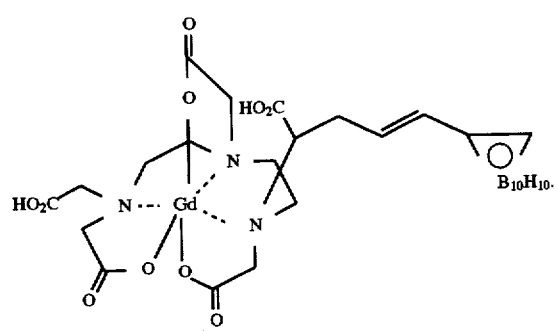

2. A gadolinium-DTPA complex containing a carborane unit represented by the following formula (2):

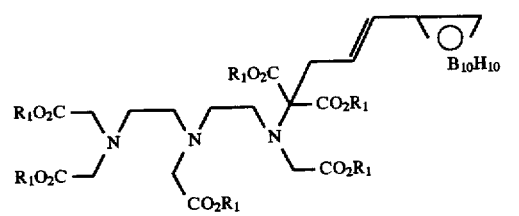

where $R_1$ is hydrogen or a lower alkyl group.

3. A carborane-containing DTPA derivative represented by the following formula (2a):

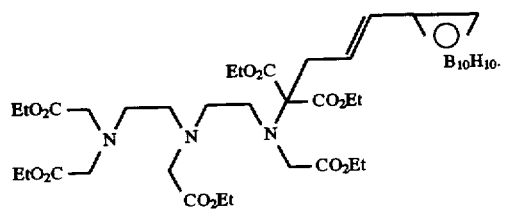

4. A carborane-containing DTPA derivative represented by the following formula (2b):

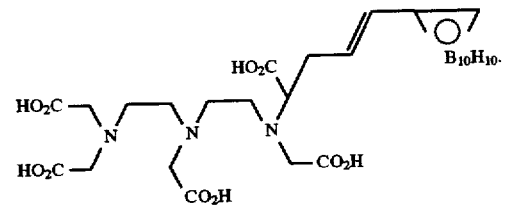

5. A method of synthesizing a gadolinium-DTPA complex containing a carborane unit represented by following formula (1):

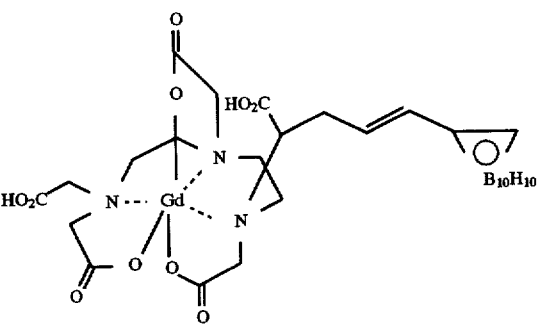

which comprises the steps of:

(a) reacting an ester derivative of DTPA represented by formula (3) and a carborane derivative represented by formula (4) in the presence of a palladium catalyst and an organic phosphine to give a carborane-containing DTPA derivative represented by formula (2c), as shown below:

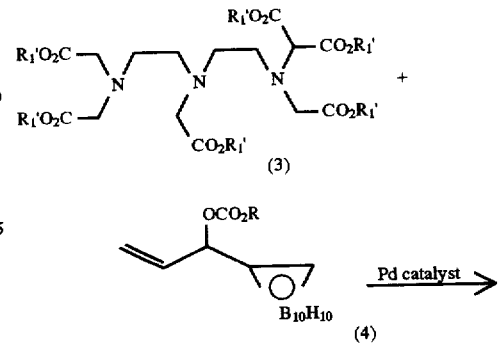

where R and $R_1'$ are a lower alkyl group;

(b) treating said carborane-containing DTPA derivative (2c) obtained in step (a) with an alkali, followed by deesterification by treatment with an acid to give a compound (2b), as shown below:

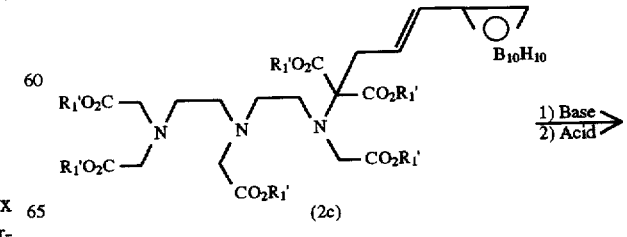

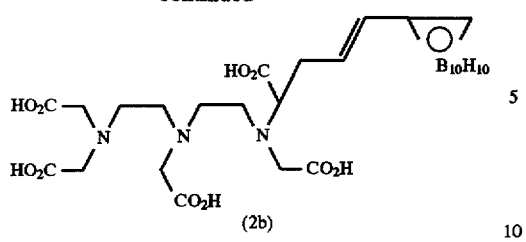

where $R_1'$ is a lower alkyl group; and (c) reacting said compound (2b) obtained in step (b) with gadolinium trichloride hexahydrate, followed by treatment with an alkali to give a compound (1) which is gadolinium-DTPA complex containing a carborane unit, as shown below:

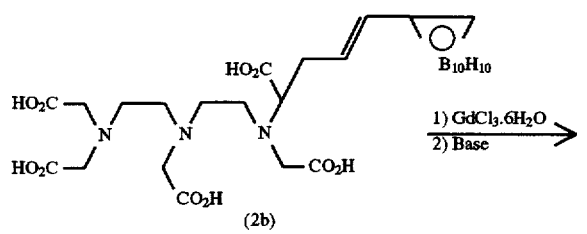

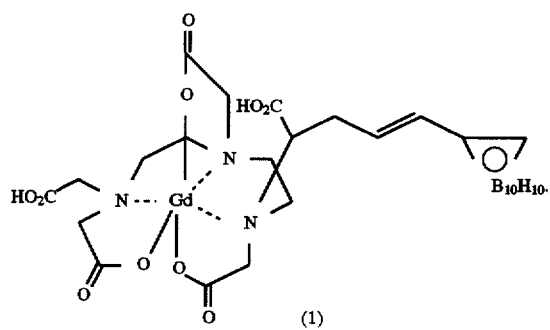

6. A method of synthesizing a carborane-containing DTPA derivative represented by formula (2c), wherein comprises the reaction of an ester derivative of DTPA represented by formula (3) with a carborane derivative represented by formula (4) in the presence of a palladium catalyst and an organic phosphine to give the carborane-containing DTPA derivative (2c), as shown below:

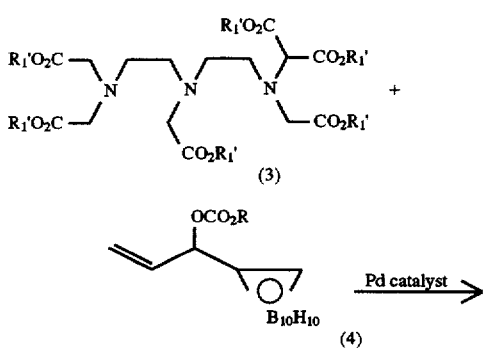

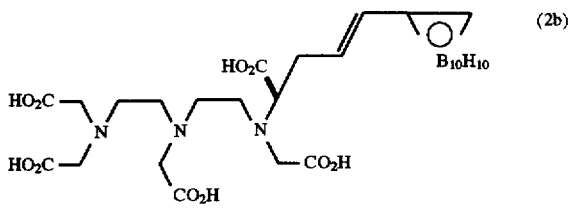

where R and $R_1'$ are a lower alkyl group.

7. A method of synthesizing a carborane-containing DTPA derivative represented by following formula (2b):

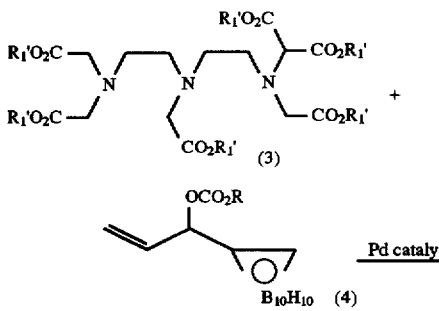

wherein comprises the steps of:

(a) reacting an ester derivative of DTPA represented by formula (3) with a carborane derivative represented by formula (4) in the presence of a palladium catalyst and an organic phosphine to give a carborane-containing DTPA derivative represented by formula (2c), as shown below:

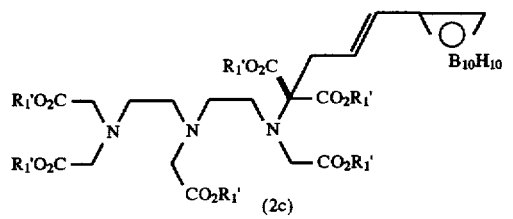

where R and $R_1'$ are a lower alkyl group; and (b) treating said carborane-containing DTPA derivative (2c) obtained in step (a) with an alkali, followed by deesterification by treatment with an acid to give a compound represented by formula (2b), as shown below:

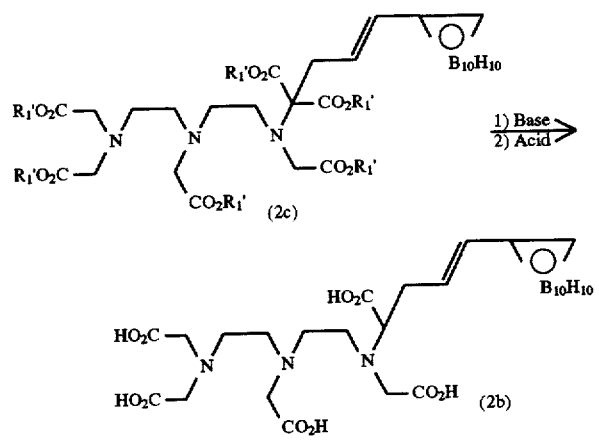

where R and $R_1'$ are a lower alkyl group.

8. The method according to any one of claims 5 to 7, wherein said palladium catalyst used is selected from the group consisting of palladium.(dibenzylideneacetone)$_2$ complex [Pd(dba)$_2$] and Pd$_2$(dba)$_3$.CHCl.

9. The method according to any one of claims 5 to 7, wherein said organic phosphine is selected from the group consisting of 1,2-bis(diphenylphosphino)ethane (dppe), triphenylphosphine, and trimethylol propanephosphite.

* * * * *